US009168378B2

(12) United States Patent
Hershey

(10) Patent No.: US 9,168,378 B2
(45) Date of Patent: Oct. 27, 2015

(54) METHODS AND DEVICES FOR TREATMENT OF NON-NEUROPATHIC CONDITIONS USING ELECTRICAL STIMULATION

(71) Applicant: BOSTON SCIENTIFIC NEUROMODULATION CORPORATION, Valencia, CA (US)

(72) Inventor: Bradley Lawrence Hershey, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/529,969

(22) Filed: Oct. 31, 2014

(65) Prior Publication Data

US 2015/0051665 A1    Feb. 19, 2015

Related U.S. Application Data

(63) Continuation-in-part of application No. 13/708,742, filed on Dec. 7, 2012, now Pat. No. 8,923,975.

(60) Provisional application No. 61/569,216, filed on Dec. 9, 2011.

(51) Int. Cl.
*A61N 1/00* (2006.01)
*A61N 1/36* (2006.01)
*A61N 1/05* (2006.01)

(52) U.S. Cl.
CPC ........ *A61N 1/36185* (2013.01); *A61N 1/36071* (2013.01); *A61N 1/36146* (2013.01); *A61N 1/36171* (2013.01); *A61N 1/0553* (2013.01); *A61N 1/36075* (2013.01); *A61N 1/36164* (2013.01)

(58) Field of Classification Search
CPC ............ A61N 1/36071; A61N 1/0536; A61N 1/0551–1/0558
See application file for complete search history.

(56) References Cited

U.S. PATENT DOCUMENTS

| | | | |
|---|---|---|---|
| 5,501,703 | A | 3/1996 | Holsheimer et al. |
| 6,181,969 | B1 | 1/2001 | Gord |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,244,150 | B1 | 7/2007 | Brase et al. |
| 7,251,529 | B2 * | 7/2007 | Greenwood-Van Meerveld ........... 607/46 |
| 7,650,184 | B2 | 1/2010 | Walter |
| 7,672,734 | B2 | 3/2010 | Anderson et al. |
| 7,742,810 | B2 | 6/2010 | Moffitt et al. |
| 7,761,165 | B1 | 7/2010 | He et al. |
| 7,949,395 | B2 | 5/2011 | Kuzma |
| 7,974,706 | B2 | 7/2011 | Moffitt et al. |
| 8,019,439 | B2 | 9/2011 | Kuzma et al. |
| 8,175,710 | B2 | 5/2012 | He |
| 8,224,450 | B2 | 7/2012 | Brase |
| 8,364,278 | B2 | 1/2013 | Pianca et al. |

(Continued)

*Primary Examiner* — Michael Kahelin
*Assistant Examiner* — Mallika D Fairchild
(74) *Attorney, Agent, or Firm* — Lowe Graham Jones PLLC; Bruce E. Black

(57) ABSTRACT

A method of treating a non-neuropathic condition includes implanting an electrical stimulation lead near a dorsolateral funiculus of a patient, the electrical stimulation lead including a plurality of stimulation electrodes; and applying electrical stimulation energy through one or more of the electrodes of the electrical stimulation lead to the dorsolateral funiculus to treat the non-neuropathic condition.

19 Claims, 7 Drawing Sheets

(56) References Cited

U.S. PATENT DOCUMENTS

| | | |
|---|---|---|
| 8,700,178 B2 | 4/2014 | Anderson |
| 8,812,115 B2 | 8/2014 | Lee |
| 8,923,975 B2 | 12/2014 | Bradley |
| 2003/0181949 A1* | 9/2003 | Whale ............................ 607/2 |
| 2007/0021802 A1 | 1/2007 | Heruth et al. |
| 2007/0142863 A1 | 6/2007 | Bradley |
| 2007/0150036 A1 | 6/2007 | Anderson |
| 2007/0168004 A1 | 7/2007 | Walter |
| 2007/0168007 A1 | 7/2007 | Kuzma et al. |
| 2008/0294226 A1 | 11/2008 | Moffitt et al. |
| 2009/0270935 A1 | 10/2009 | Zhao et al. |
| 2010/0324630 A1 | 12/2010 | Lee et al. |
| 2011/0009923 A1 | 1/2011 | Lee |

* cited by examiner

METHODS AND DEVICES FOR TREATMENT OF NON-NEUROPATHIC CONDITIONS USING ELECTRICAL STIMULATION

FIELD

The present invention relates to tissue stimulation systems, and more particularly, to spinal cord stimulation systems, for use in treating non-neuropathic conditions including disease and disorders. In addition, the present invention is directed to treating inflammation conditions, diseases, and disorders using electrical stimulation.

BACKGROUND

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic neuropathic pain syndromes, and the application of spinal cord stimulation has expanded to include additional applications, such as angina pectoralis, peripheral vascular disease, and incontinence, among others. Spinal cord stimulation is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further include a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Programmed electrical pulses can be delivered from the neurostimulator to the stimulation lead(s) to stimulate or activate a volume of the spinal cord tissue. In particular, electrical stimulation energy conveyed to the electrodes creates an electrical field, which, when strong enough, depolarizes (or "stimulates") the neural fibers within the spinal cord beyond a threshold level, thereby inducing the firing of action potentials (APs) that propagate along the neural fibers to provide the desired efficacious therapy to the patient.

SCS may be utilized to treat patients suffering from chronic neuropathic pain. To this end, electrical stimulation is generally applied to the dorsal column (DC) nerve fibers, which is believed to inhibit the perception of pain signals via the gate control theory of pain by creating interneuronal activity within the dorsal horn that inhibits pain signals traveling from the dorsal root (DR) neural fibers that innervate the pain region of the patient up through the dorsolateral funiculus of the spinal cord to the brain. Consequently, stimulation leads are typically implanted within the dorsal epidural space to provide stimulation to the DC nerve fibers. Such techniques of treating pain may be beneficial for some patients initially, but it has decreasing efficiency over time. This may be because the natural neural interconnections may be minimally present in some patients, or because the natural neural interconnections may be rendered ineffective by the pathological condition.

BRIEF SUMMARY

One embodiment is a method of treating a non-neuropathic condition that includes implanting an electrical stimulation lead near a dorsolateral funiculus of a patient, the electrical stimulation lead including a plurality of stimulation electrodes; and applying electrical stimulation energy through one or more of the electrodes of the electrical stimulation lead to the dorsolateral funiculus to treat the non-neuropathic condition. In at least some embodiments, the method also includes increasing an activation threshold of a side-effect exhibiting neural structure relative to an activation threshold of the dorsolateral funiculus of the patient, wherein the electrical stimulation energy is applied to the dorsolateral funiculus of the patient while the activation threshold of the neural structure relative to the dorsolateral funiculus is increased, thereby treating the non-neuropathic condition without stimulating the neural structure.

Another embodiment is a method of treating a non-neuropathic condition that includes applying electrical stimulation energy to a dorsolateral funiculus of a patient through one or more electrodes of an implanted electrical stimulation lead to treat the non-neuropathic condition; and increasing an activation threshold of a side-effect exhibiting neural structure relative to an activation threshold of the dorsolateral funiculus of the patient, wherein the electrical stimulation energy is applied to the dorsolateral funiculus of the patient while the activation threshold of the neural structure relative to the dorsolateral funiculus is increased, thereby treating the non-neuropathic condition without stimulating the neural structure.

Yet another embodiment is a method of treating an inflammatory condition that includes applying electrical stimulation energy to a dorsolateral funiculus of a patient using an implanted electrical stimulation lead to treat the inflammatory condition.

In at least some embodiments, applying electrical stimulation energy includes applying the electrical stimulation energy as a time-varying electrical energy having a frequency in a range of 2 to 30 kHz. In at least some embodiments of the methods, the non-neuropathic condition is an inflammatory condition. In at least some embodiments of the methods, the inflammatory condition includes inflammation of a spinal cord of the patient. In at least some embodiments of the methods, the inflammatory condition is selected from spondyloarthritis, spondylarthropathy, or lower back pain arising from spinal cord inflammation. In at least some embodiments of the methods, the inflammatory condition includes inflammation of a region of the patient peripheral to a spinal cord of the patient. In at least some embodiments of the methods, the inflammatory condition is selected from fibromyalgia, migraine headache, irritable bowel syndrome, ankylosing spondylitis, Crohn's disease, rheumatoid arthritis, osteoarthritis, or other arthritis of one or more joints.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention relates to tissue stimulation systems, and more particularly, to spinal cord stimulation systems, for use in treating non-neuropathic conditions including disease and disorders. In addition, the present invention is directed to treating inflammation conditions, diseases, and disorders using electrical stimulation.

Figure 1:
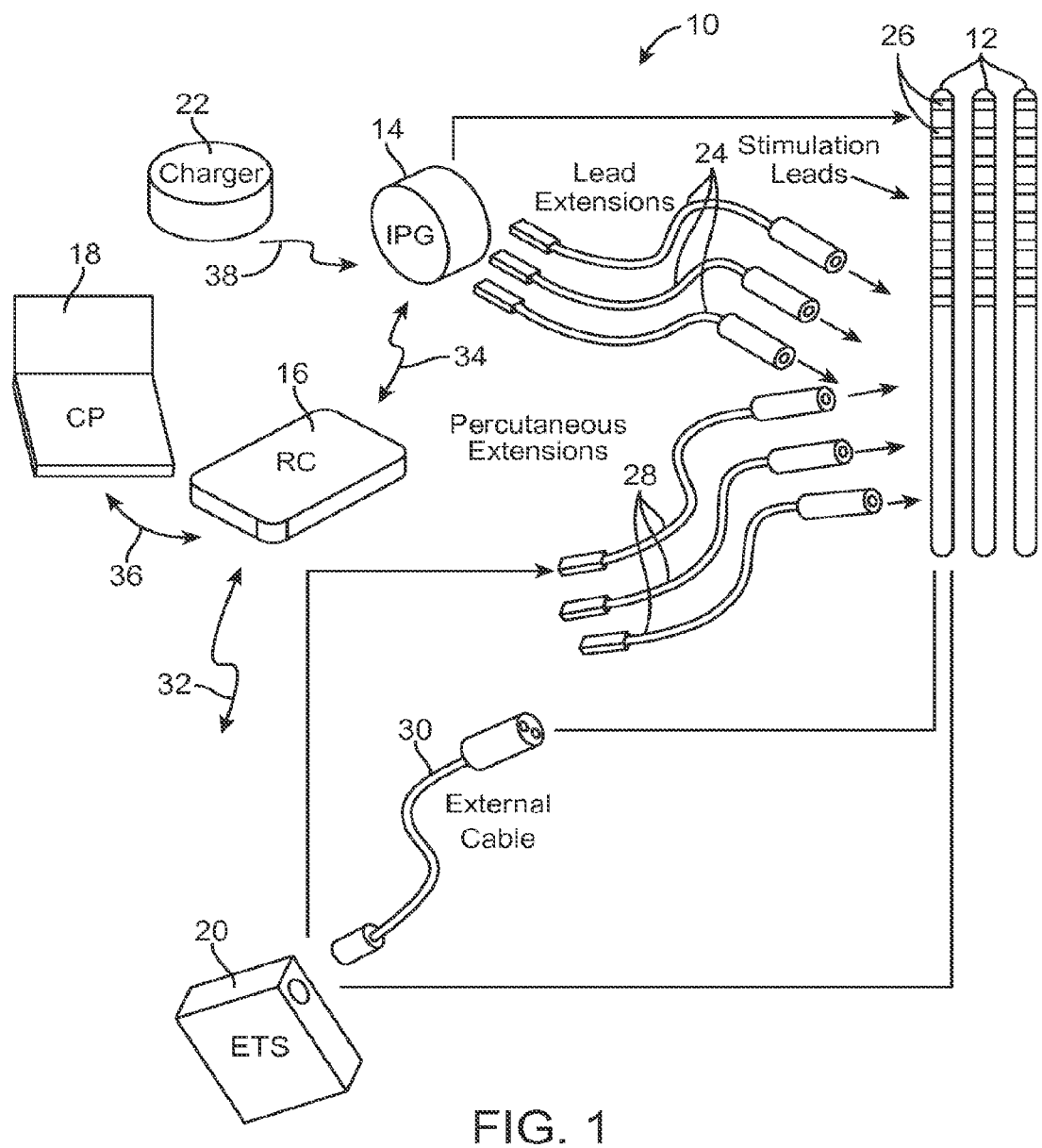
FIG. 1 is a plan view of a Spinal Cord Stimulation (SCS) system constructed in accordance with one embodiment of the present inventions.

Turning first to FIG. 1, an exemplary SCS system 10 includes one or more stimulation leads 12 (in the illustrated case, three) and an implantable pulse generator (IPG) 14 (or alternatively RF receiver-stimulator). The system 10 can also include one or more of an external remote control RC 16, a Clinician's Programmer (CP) 18, an External Trial Stimulator (ETS) 20, and an external charger 22.

The IPG 14 is physically connected, optionally via one or more lead extensions 24, to the stimulation lead(s) 12. Each lead carries multiple electrodes 26 arranged in an array. The stimulation leads 12 are illustrated as percutaneous leads in FIG. 1, although as will be described in further detail below, a surgical paddle lead can be used in place of the percutaneous lead(s). As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected, optionally via the percutaneous lead extensions 28 and external cable 30, to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. One difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, all of which are incorporated by reference.

Figure 2:
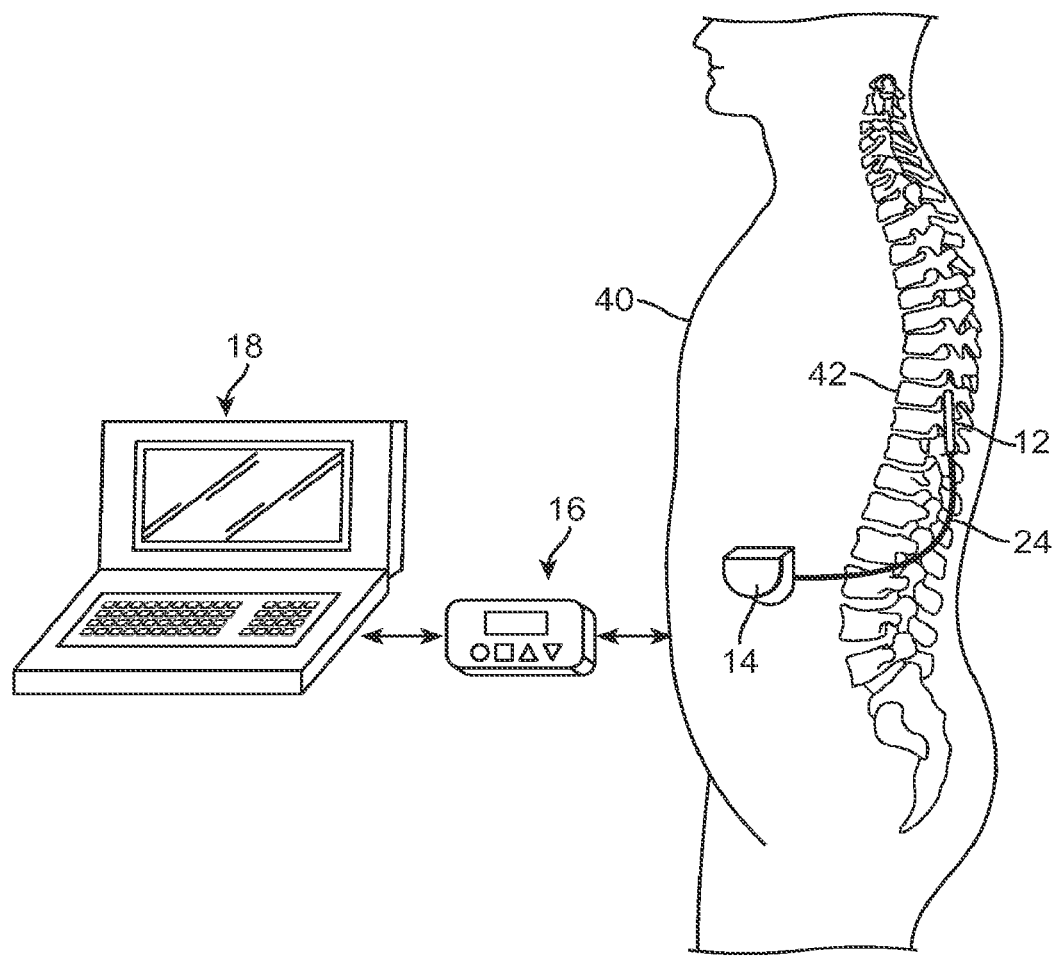
FIG. 2 is a plan view of the SCS system of FIG. 1 in use within a patient.

As shown in FIG. 2, the stimulation leads 12 are implanted within the spinal column 42 of a patient 40. The preferred placement of the electrode leads 12 is adjacent, i.e., resting upon, the spinal cord area to be stimulated. Due to the lack of space near the location where the electrode leads 12 exit the spinal column 42, the IPG 14 is generally implanted in a surgically-made pocket, for example, either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
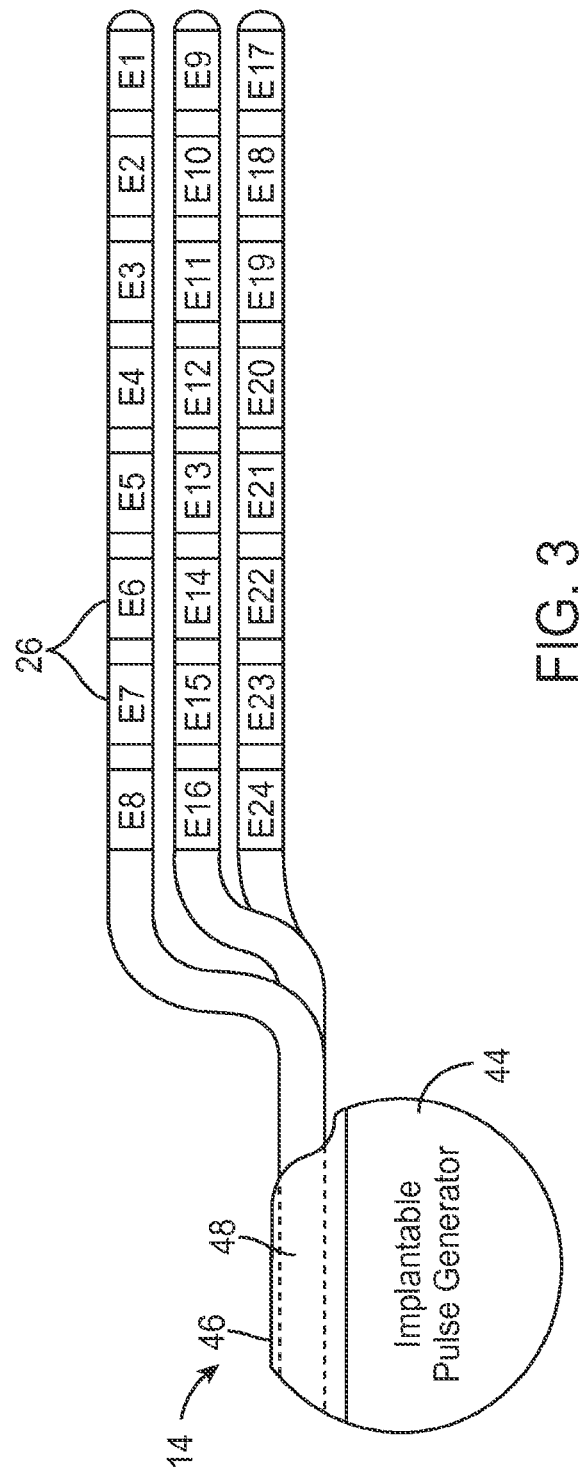
FIG. 3 is a plan view of an implantable pulse generator (IPG) and three percutaneous stimulation leads used in the SCS system of FIG. 1.

Referring now to FIG. 3, the external features of the stimulation leads 12 and the IPG 14 will be briefly described. Each of the illustrated stimulation leads 12 has eight electrodes 26 (respectively labeled E1-E8, E9-E16, and E17-E24). The actual number and shape of leads and electrodes will, of course, vary according to the intended application. Additional examples of the constructions and methods of manufacturing percutaneous stimulation leads are disclosed in the patents and patent applications cited above and in U.S. Pat. Nos. 8,019,439 and 7,650,184, both of which are expressly incorporated herein by reference.

Figure 4:
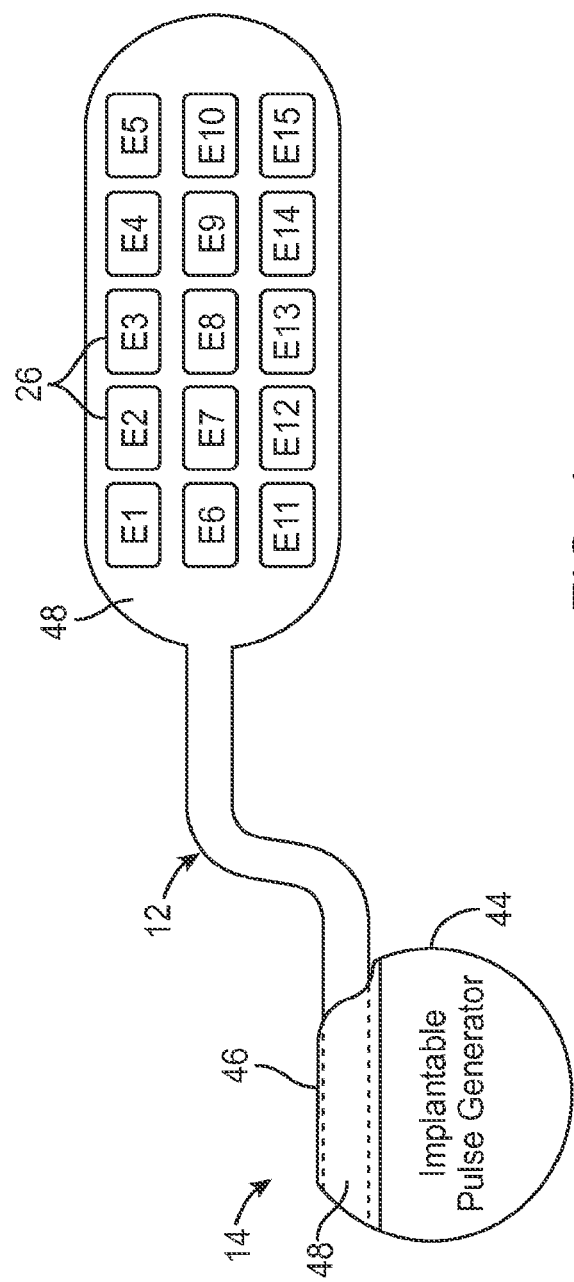
FIG. 4 is a plan view of an implantable pulse generator (IPG) and a surgical paddle lead used in the SCS system of FIG. 1.

Alternatively, as illustrated in FIG. 4, the stimulation lead 12 takes the form of a surgical paddle lead on which electrodes 26 are arranged in a two-dimensional array in, for example, three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Additional examples of the constructions and methods of manufacture of surgical paddle leads are disclosed in the patents and patent applications cited above and in U.S. Pat. No. 8,700,178, which is expressly incorporated herein by reference.

In each of the embodiments illustrated in FIGS. 3 and 4, the IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes one or more ports (three ports 44 or three percutaneous leads or one port for the surgical paddle lead) for receiving the proximal end(s) of the stimulation lead(s) 12. In the case where the lead extensions 24 are used, the port(s) 44 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and the case 40. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5:
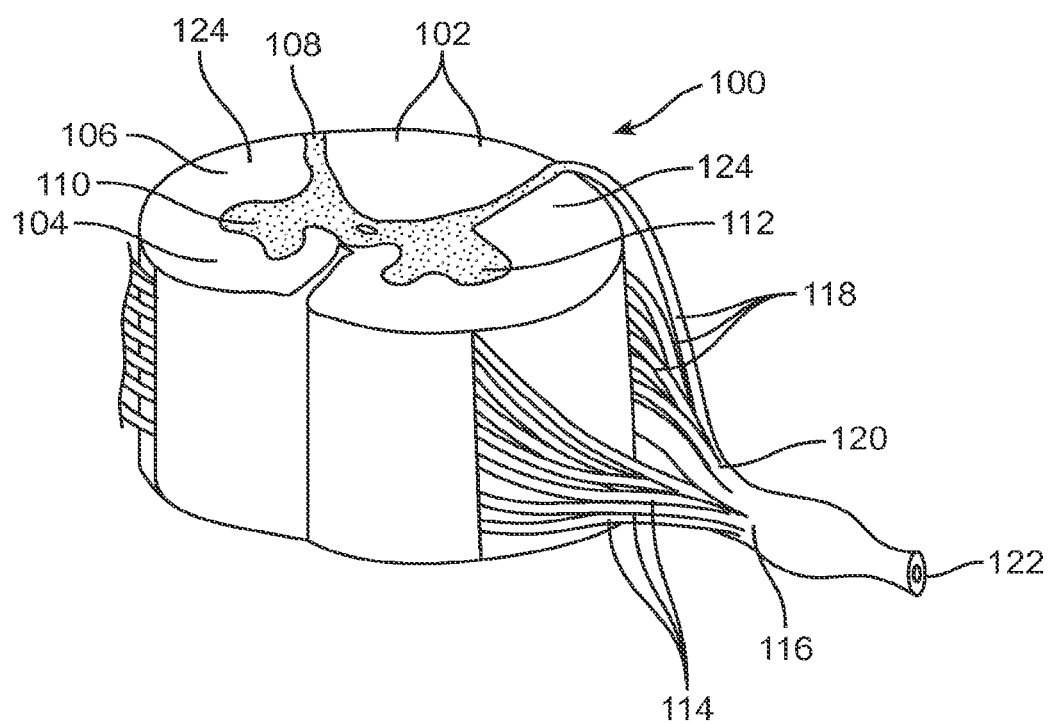
FIG. 5 is a peripheral view of the spinal cord and spinal nerves.
Figure 6:
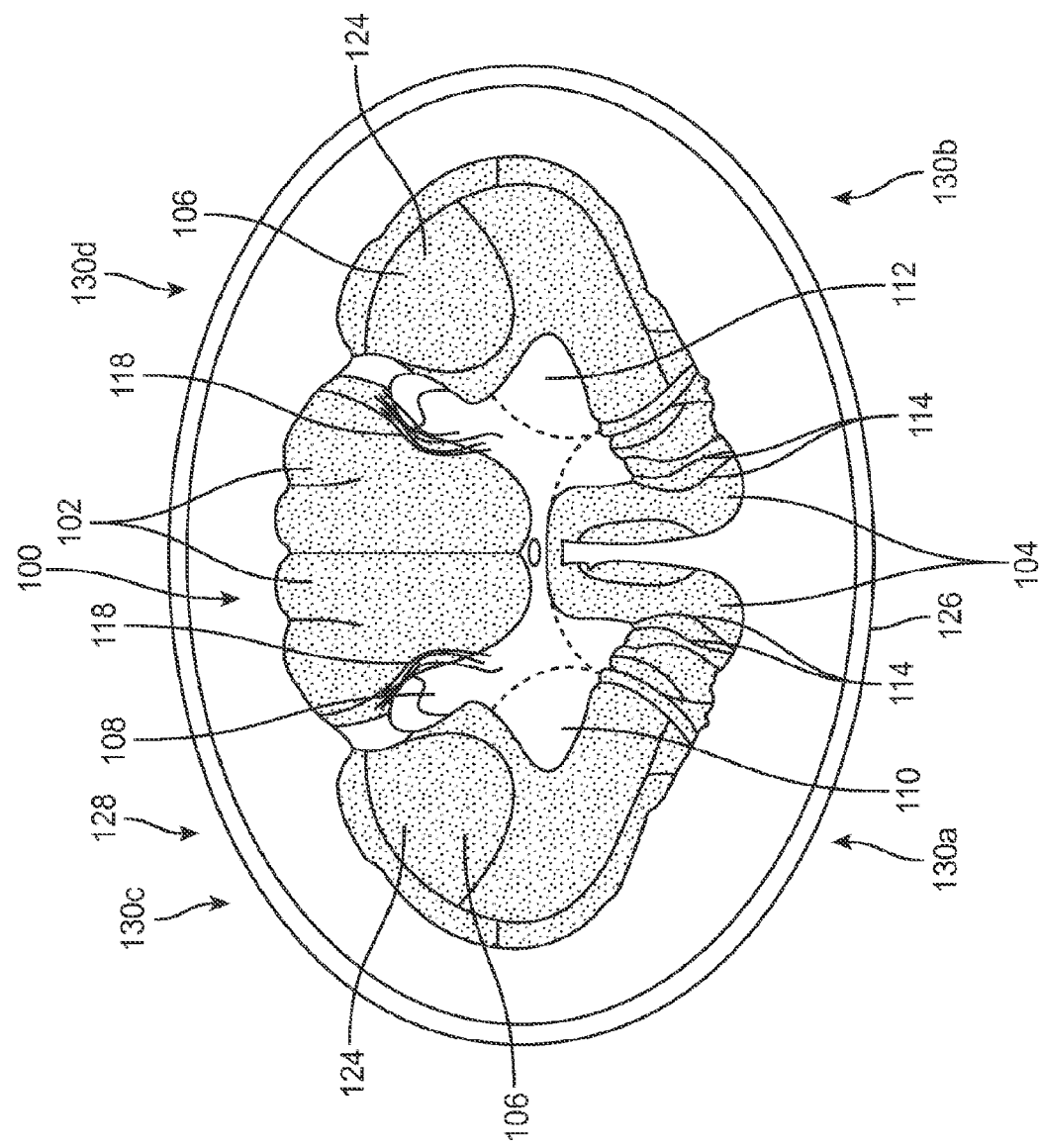
FIG. 6 is a cross-sectional view of the spinal cord.

Referring now to FIGS. 5 and 6, portions of the spinal cord 100 are described. The spinal cord 100 is divided into three columns: the dorsal column 102, the ventral column 104, and the lateral column 106. Similarly, the butterfly-shaped gray matter of the spinal cord 100 is divided into the dorsal horn 108, the ventral horn 110, and the lateral horn 112.

A group of motor nerve rootlets (ventral root (VR) nerve fibers) 114 branch off of the ventral horn 110 and combine to form the ventral root 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerves 122, which innervate peripheral regions (e.g., arms, legs, etc.) of the patient's body. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5.

The dorsolateral funiculus 124 is a neural pathway lying in the dorsolateral region of the spinal cord, and is included within the lateral column 106. The dorsolateral funiculus 124 contains several functioning ascending and descending tracts, including the dorsospinocerebellar tract, which controls proprioceptionl; the spinocervical tract, which controls coarse mechanoreception; the corticospinal tract, which controls voluntary and fine motor control; and the descending inhibitory tract, which controls pain transmission. It is known that the supraspinal centers, including the periaqueductal grey, periventricular gray, rostroventral medulla/nucleus raphe magnus, and anterior pretectal nucleus, manages the descending inhibition of pain via release of serotonin, norepinephrine, and enkephalin in the dorsal horn. The descending inhibitory tract of the dorsolateral funiculus 124, which includes relatively large diameter nerve tracts and thus is easily stimulated, runs along the outer surface of the dorsolateral funiculus 124. Thus, the descending inhibitory tract of the dorsolateral funiculus 124 offers an attractive target for managing pain. The spinal cord 100 is enclosed by a dura mater 126, with an epidural space 128 surrounding the dura mater 126. The epidural space 128 may be topologically divided into four quadrants: a left ventral-lateral quadrant 130a, a right ventral-lateral quadrant 130b, a left dorsal-lateral quadrant 130c, and a right dorsal-lateral quadrant 130d.

In conventional SCS techniques, stimulation is applied to the dorsal column 102 of the spinal cord 100 to treat chronic neuropathic pain, and accordingly, stimulation leads are positioned in the dorsal region of the epidural space 128. As opposed to the conventional systems, the embodiments of the present invention modulate the dorsolateral funiculus 124 of the spinal cord 100 for treating disorders such as chronic neuropathic pain.

Surprisingly, it has also been found that the dorsolateral funiculus can also be electrically stimulated to treat non-neuropathic conditions. For example, the dorsolateral funiculus can be electrically stimulated to treat inflammatory conditions and the pain associated with such conditions. As an example, spondyloarthritis (or spondyloarthropathy) is a family of inflammatory rheumatic diseases that cause arthritis and can result in lower back pain. Electrical stimulation of the dorsolateral funiculus of the spinal cord can be used to treat this condition and reduce or eliminate the lower back pain.

Moreover, the inflammatory condition to be treated need not be located in the spinal region. Electrical stimulation of the dorsolateral funiculus can be used to treat inflammatory conditions in tissues outside, or extending beyond, the spinal cord (for example, peripheral inflammatory pain) including the treatment of inflammatory conditions (or conditions which have inflammation associated with the disease or disorder) such as fibromyalgia, migraine headaches, irritable bowel syndrome, arthritis of the joints, osteoarthritis, rheumatoid arthritis, Crohn's disease, ankylosing spondylitis, and the like. Stimulation of the dorsolateral funiculus can release neurotransmitters or endogenous opioids (or any combination thereof) that reduce or eliminate the pain associated with inflammation.

To stimulate the dorsolateral funiculus, one or more stimulation leads are implanted near the dorsolateral funiculus. In at least some embodiments, the stimulation lead(s) 12 are implanted within the patient lateral to the midline of the spinal cord 100 within the epidural space 128, such that the tip(s) of the stimulation lead(s) 12, and thus some of the electrodes 26, are located in either of the dorsal-lateral quadrants 130$c$, 130$d$ of the epidural space 128 adjacent the dorsolateral funiculus 124 of the spinal cord 100.

Thus, electrical stimulation energy can be epidurally applied by the stimulation lead(s) to stimulate the dorsolateral funiculus 124, thereby treating the non-neuropathic condition to reduce or eliminate one or more symptoms of the condition such as, for example, pain associated with the condition. The distal end(s) of the stimulation lead(s) 12 are preferably located at a position along the spinal cord 100 rostral to the dorsal root 120 that innervates the pain region of the patient. In this manner, electrical stimulation occurs at the region of the dorsolateral funiculus 124 that is rostral to this innervating dorsal root 120, such that inhibitory signals generated are conveyed to the region of the dorsal horn associated with the particular innervating dorsal root 120. The descending pain inhibitory tract is located on the outer surface of the dorsolateral funiculus 124, and therefore, more easily stimulated than the other tracts within the dorsolateral funiculus 124. In at least some embodiments, however, if the magnitude of the stimulation is too high, it is possible that the neural axons of the spinocerebellar tracts may be inadvertently stimulated which may result in side effects in the form of involuntary motor movements. If this occurs, the stimulation amplitude may be turned down such that electrical field modulation of the dorsolateral funiculus 124 occurs without necessarily creating a preponderance of action potentials in the neural axons of the dorsolateral funiculus 124.

In at least some embodiments, during application of the stimulation energy to the dorsolateral funiculus 124, the activation threshold of neural structures (e.g., the DR nerve fibers 118 under which the dorsolateral funiculus 124 generally lies) relative to the activation threshold of the dorsolateral funiculus 124 is preferably increased, so that those neural structures are not inadvertently stimulated. Different techniques can be used to increase the activation thresholds of these neural structures relative to the activation threshold of the dorsolateral funiculus 124. In at least some embodiments, for example, the stimulation leads(s) 12 are located within the cervical region of the spinal cord, where the sensitive DR nerve fibers 118 extend straight out from the spinal cord 100, thereby providing more spatial isolation between these nerve fibers and the dorsolateral funiculus 124. As such, the distal tip(s) of the stimulation lead(s) 12 may be more easily located between the DR nerve fiber grouping 116.

Figure 7:
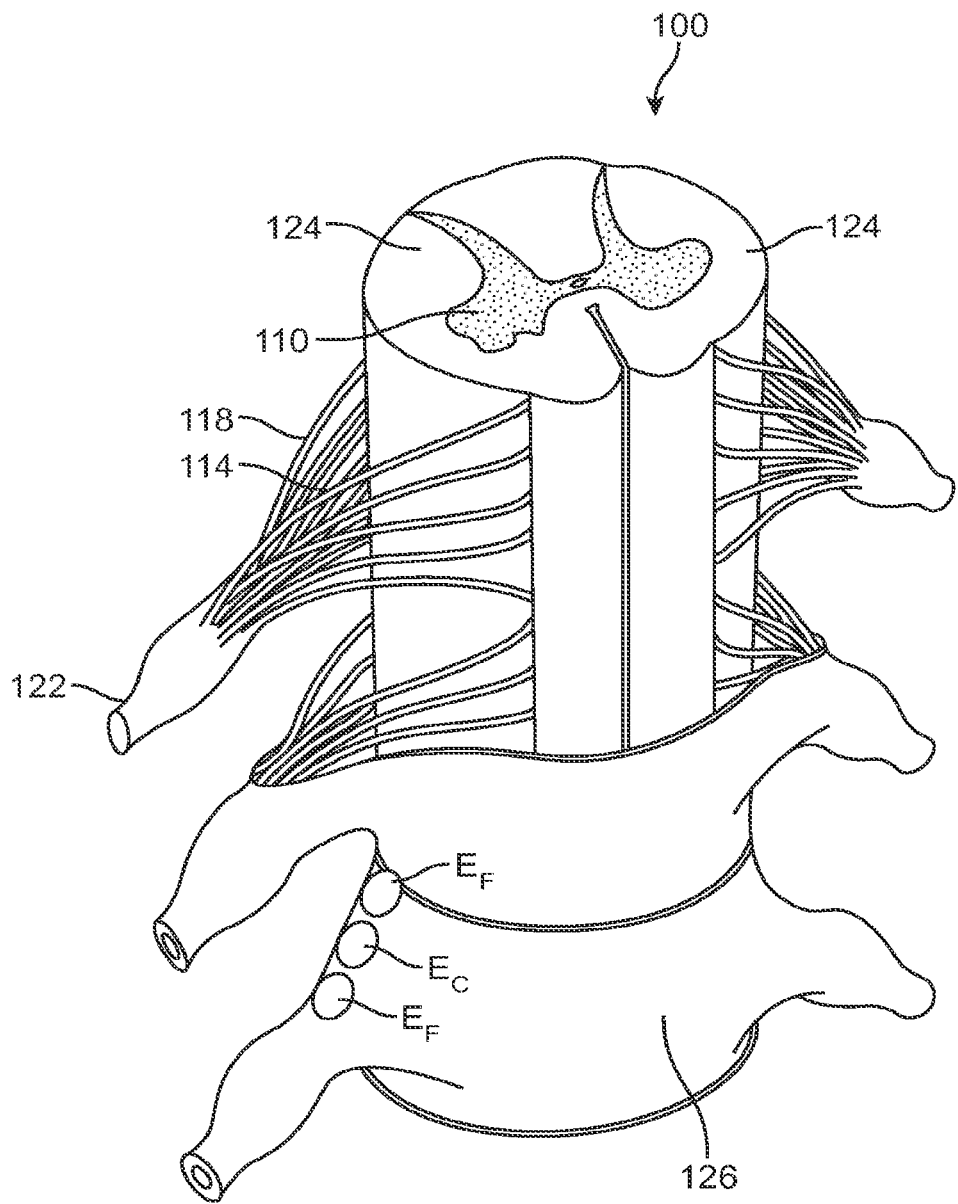
FIG. 7 is a perspective view showing one electrode arrangement relative to the spinal cord and spinal nerves in accordance with the present invention.

In at least some embodiments, referring to FIG. 7, a configuration of three electrodes (labeled $E_C$ for the center electrode, and $E_F$ for the flanking electrodes) on one or more leads may be arranged relative to a pair of adjacent DR nerve fiber groupings 116, such that the three electrodes are aligned along the longitudinal axis of the spinal cord 100 (i.e., in the rostro-caudal direction) between the DR nerve groupings 118, such that the flanking electrodes $E_F$ of the tripole configuration are respectively closest to the DR nerve fiber groupings 118. Optionally, e.g., in the case of bilateral pain, another configuration of three electrodes can be aligned along the longitudinal axis of the spinal cord 100 between the DR nerve fiber groupings 118 at the same spinal level on the other lateral side of the spinal cord 100. The electrode configurations can be formed, e.g., using the distal-most electrodes 26 on three side-by-side percutaneous leads 12 (shown in FIG. 3) or a row of electrodes 26 on the surgical paddle lead 12 (shown in FIG. 4) or on a single percutaneous lead.

In as least some embodiments, the electrodes 26 may be configured in a manner that increases the activation threshold of the DR nerve fiber groupings 118 relative to the activation threshold of the dorsolateral funiculus 124 in order to reduce or inhibit the stimulation of DR nerve fiber groupings 118 when the dorsolateral funiculus 124 is stimulated.

In at least some embodiments, the objective is to apply electrical suppression energy to the DR nerve fiber groupings 118 to decrease their activation threshold. The electrodes 26 can be placed as close to the spinal cord 100 in order to increase or maximize the resolution of the energy transmitted by the electrodes 26; that is, to focus the stimulating effect of the stimulation energy on a target site in the dorsolateral funiculus 124, and to focus the activation threshold increasing effect of the suppression energy on the DR nerve fiber groupings 118. In at least some embodiments, the proximity of the electrodes 26 to the spinal cord 100 is less than one-half of the distance between adjacent electrodes 26. Because the electrodes 26 are typically separated from the spinal cord by the dura 126 and spinal cord fluid, there will typically be some distance between the electrodes 26 and the spinal cord 100, with the distance varying from patient to patient. If implanted within the cervical region of the spine, the proximity of the electrodes 26 to the spinal cord 100 can be quite small, and therefore, high resolution can be achieved. If implanted within the thoracic region of the spine, the electrodes 26 are often further from the spinal cord 100, and therefore, a lower resolution may be achieved.

In one technique for preventing inadvertent stimulation of the DR nerve fiber groupings 118, the electrodes are configured as a tripole, such that the flanking electrodes $E_F$ adjacent the two DR nerve fiber groupings 118 are anodes, and the center electrode $E_C$ is a cathode. In this configuration, electrical stimulation energy conveyed between the cathode and anode(s) creates an electrical field that stimulates the dorsolateral funiculus 124, while preventing or reducing stimulation of the DR nerve fiber groupings 118. The electrical current sourced by the outer flanking electrodes $E_F$ hyperpolarizes the DR nerve fiber groupings 118, thereby decreasing their activation threshold, while the electrical current sunk by the center electrode $E_C$ depolarizes the nerve fibers in the dorsolateral funiculus 124, thereby creating a locus of stimulation that is confined to the region of the dorsolateral funiculus 124 adjacent the center electrode $E_C$. In effect, the center electrode $E_C$ generates the electrical stimulation energy at the dorsolateral funiculus 124, while the flanking electrodes $E_F$ "push" the electrical stimulation energy away from the DR nerve fiber groupings 118.

In at least some embodiments, it is desirable that the locus of stimulation be narrow without increasing its depth, thereby stimulating target nerve fibers within the dorsolateral funiculus, while reducing (compared to single electrode stimulation) or preventing stimulation of the DR nerve fiber groupings 118. Further narrowing may require an increase in the electrical current sourced at the flanking electrodes $E_F$, but this may result in an increase in the current sunk by the center electrode $E_C$, thereby increasing the depth of the locus of stimulation, which may lead to undesirable outcomes (e.g., discomfort or undesirable reflexive activity). As such, a portion of the electrical current sourced at the flanking electrodes $E_F$ can be additionally sunk at a remote electrode (e.g., the case of the IPG or even another electrode (on the same or different lead) remote from the tripole configuration), thereby creating a local current imbalance at the target site of the dorsolateral funiculus 124.

Further examples of the use of tripolar electrode arrangements to render tissue less excitable to subsequent stimulation are disclosed in U.S. Patent Application Publication No. 2007/0142863, which is expressly incorporated herein by reference.

In another technique for reducing or preventing inadvertent stimulation of the DR nerve fiber groupings 118, a sub-threshold, hyperpolarizing conditioning pre-pulse can be applied by flanking electrodes $E_F$ to the adjacent DR nerve fiber groupings 118, and a depolarizing stimulation pulse can be subsequently applied by the center electrode $E_C$ to the dorsolateral funiculus 124. The temporal separation between the end of the conditioning pulse and the beginning of the stimulation pulse can be zero and is preferably less than 100 µs, and more preferably, less than 30 µs. The conditioning pre-pulse preferably has a relatively short duration, preferably less than 200 µs, more preferably less than 150 µs, and most preferably less than 75 µs, such that m-gates of the sodium ion channels in the neural axons are closed to render the tissue less excitable to subsequent stimulation. The stimulation pulse preferably has a relatively short duration, e.g., less than 200 µs. Optionally, a relatively long depolarizing conditioning pulse preceding the relatively short hyperpolarizing conditioning pulse can be applied by the flanking electrodes $E_F$, such that h-gates of the sodium ion channels in the neural axons are closed to render the tissue even less excitable to subsequent stimulation. In at least some embodiments, to determine the amplitude for the conditioning pre-pulse(s), the amplitude level of the stimulation pulse may be incrementally increased until a side-effect is experienced by the patient, and for each incremental increase in the stimulation pulse, the amplitude of the conditioning pre-pulse(s) may be increased until the side-effect is eliminated or minimized.

Further examples of the use of conditioning pre-pulses to render tissue less excitable to subsequent stimulation are disclosed in U.S. Pat. No. 7,742,810, which is expressly incorporated herein by reference.

In another technique for reducing or preventing inadvertent stimulation of the DR nerve fiber groupings 118, electrical background energy is conveyed from the flanking electrodes $E_F$ in accordance with at least one stochastic parameter. If the electrical background energy is in the form of pulses, the stochastic parameter may include at least one of an interpulse interval, pulse amplitude, pulse shape, and pulse duration. If the electrical background energy is white noise, the stochastic parameter may be a frequency.

The three electrodes can be configured as stimulating electrodes in a tripolar arrangement (center electrode $E_C$ as the cathode, and flanking electrodes $E_F$ as the anodes) in a manner described above, while the flanking electrodes $E_F$ can be configured as background electrodes in a monopolar arrangement with the IPG case 40. Thus, electrical stimulation energy is conveyed between the tripolar arrangement of the electrodes, thereby therapeutically stimulating dorsolateral funiculus, and electrical background energy is conveyed between the flanking electrodes $E_F$ and the IPG case 40, thereby decreasing the excitability of the DR nerve fiber groupings 118.

Notably, due to the monopolar arrangement, the field strength of the electrical background energy conveyed from the flanking electrodes $E_F$ decays at a relatively low rate with distance. As such, the flanking electrodes $E_F$ may be relatively far from the DR nerve fiber groupings 118 for them to modulate the excitability of the DR nerve fiber groupings 118. Alternatively, the electrical background energy may be conveyed from flanking electrodes $E_F$ in a bipolar arrangement. However, in this case, due to current shunting, the flanking electrodes $E_F$ are relatively close to the DR nerve fiber groupings 118. In either case, as a general rule, the excitability of the DR nerve fiber groupings 118 will be decreased if the magnitude of the electrical background energy is relatively high. Alternatively, electrical background energy with a relatively low magnitude may be conveyed from the center electrode $E_C$, thereby increasing the excitability of the dorsolateral funiculus 124. In effect, the activation threshold of the DR nerve fiber groupings 118 will be increased relative to the activation threshold of the dorsolateral funiculus 124 by decreasing the activation threshold of the dorsolateral funiculus 124.

Because the excitability of the DR nerve fiber groupings 118 can be decreased by the electrical background energy, the effect that the inadvertent conveyance of the electrical stimulation energy to the DR nerve fiber groupings 118 can be decreased. In one method, the electrical background energy is set equal to or higher than 10% of the perception threshold of the patient. Preferably, the electrical background energy is sub-threshold (i.e., does not stimulate nerve fibers), but may be supra-threshold if it provides therapy to the patient or can otherwise be tolerated by the patient. Ultimately, the magnitudes of the electrical stimulation energy and electrical background energy can be set relative to each other through trial and error.

Further examples of the use of electrical background energy to render tissue less excitable to subsequent stimulation are disclosed in U.S. Pat. No. 8,812,115, which is expressly incorporated herein by reference.

In yet another technique for reducing or preventing inadvertent stimulation of the DR nerve fiber groupings 118, which works particularly well if the DR nerve fiber groupings 118 extend over the targeted stimulation site of the dorsolateral funiculus 124 (e.g., in the thoracic region), and are therefore closer to the stimulating electrode(s) than the target site of the dorsolateral funiculus 124, the electrical stimulation energy takes the form of high frequency (e.g., in the range of 2-30 KHz) time-varying electrical energy (e.g., a sinusoidal energy), the frequency and amplitude of which may be selected to increase the activation threshold of the relatively close neural structure (in this case, the DR nerve fiber groupings 118), while stimulating the relatively far neural structure (in this case, the dorsolateral funiculus 124).

This ability is due, in large part, because the blocking threshold of a nerve fiber by high frequency electrical energy is higher than the threshold at which the nerve fiber is activated by the same high frequency electrical energy. Thus, if the high frequency electrical energy has an amplitude that is higher than the blocking threshold of relatively close nerve fibers, the relatively far nerve fibers at a particular depth will still have a blocking threshold above the amplitude of the high frequency electrical energy, but a stimulation threshold below the amplitude of the high frequency electrical energy. This means that relatively close nerve fibers will be blocked at a stimulation current that activates relatively far nerve fibers.

The desired depth range of blocked nerve fibers and the desired depth range of the stimulated nerve fibers may be tuned by selecting the amplitude and frequency of the high frequency electrical energy. In general, as the amplitude of the high frequency electrical energy is increased, the range of distance in which neural structures are blocked increases, and the range of distance in which the neural structures are stimulated decreases.

In one embodiment for determining the amplitude for the high frequency electrical energy, the stimulation amplitude may be increased until the patient reports a segmental effect (e.g., paresthesia) from the stimulation, ostensibly due to activation of the DR nerve fibers 118. Then, the stimulation amplitude may be increased until the patient reports the segmental effect ceases or is negligible. This stimulation amplitude represents the minimum level for therapy. The stimulation amplitude may then be further increased until direct motor activity is segmentally experienced by the patient, ostensibly due to direct activation of the VR nerve fibers 114. This stimulation amplitude represents the maximum level for therapy. The patient may then be free to adjust the stimulation amplitude between these minimum and maximum limits. When stimulation is turned on from an off-state, the stimulation amplitude may be gradually ramped up to minimize the onset of stimulating the sensitive neural structures.

Further examples of the use of high frequency electrical energy to block action potentials in closer neural tissue while stimulating further neural tissue are disclosed in U.S. Patent Application Publication No. 2010/0324630, which is expressly incorporated herein by reference.

Optionally, one or more sensors, such as sense amplifiers, accelerometers, chemical sensors, or thermal sensors, may be employed to ensure that the stimulation applied is efficacious or to identify side effects arising from stimulation activity. For example, a sense amplifier coupled to the electrodes 26 may detect ventral or dorsal root activity and subsequently, the stimulation output may be altered to reduce dorsal or ventral root activity.

It should be understood that the SCS system 10 may be utilized alone or in conjunction with other known implantable devices, such as vagal stimulators, pacemakers, defibrillators, sympathetic chain stimulators, brains stimulators, and so on. The SCS system 10 may interact with other stimulator systems, and in one embodiment, all the stimulator systems may be contained within a single system. In such embodiments, the stimulation source and mechanism to control and/or modify stimulation may be applied through a common source. For example, the SCS system 10 may have multiple leads enabling multiple purposes, e.g., an additional stimulation lead or leads positioned over the dorsal column to provide conventional stimulation.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed as new and desired to be protected by Letters Patent of the United States is:

1. A method of treating a non-neuropathic condition, the method comprising:

implanting an electrical stimulation lead in an epidural space of a patient near a dorsolateral funiculus of the patient, the electrical stimulation lead comprising a plurality of stimulation electrodes, wherein the electrical stimulation lead is implanted with at least three of the stimulation electrodes disposed lateral of a midline of a spinal cord of the patient in a selected single dorsal-lateral quadrant of the epidural space and adjacent the dorsolateral funiculus of the patient; and applying electrical stimulation energy through one or more of the at least three of the stimulation electrodes of the electrical stimulation lead to the dorsolateral funiculus to treat the non-neuropathic condition.

2. The method of claim 1, wherein applying electrical stimulation energy comprises applying electrical stimulation energy through the stimulation electrodes of the electrical stimulation lead to the dorsolateral funiculus to reduce pain arising from the non-neuropathic condition.

3. The method of claim 1, wherein the non-neuropathic condition is an inflammatory condition.

4. The method of claim 3, wherein the inflammatory condition comprises inflammation of a spinal cord of the patient.

5. The method of claim 4, wherein the inflammatory condition is selected from spondyloarthritis, spondylarthropathy, or lower back pain arising from spinal cord inflammation.

6. The method of claim 3, wherein the inflammatory condition comprises inflammation of a region of the patient peripheral to a spinal cord of the patient.

7. The method of claim 6, wherein the inflammatory condition is selected from fibromyalgia, migraine headache, irritable bowel syndrome, ankylosing spondylitis, Crohn's disease, rheumatoid arthritis, osteoarthritis, or other arthritis of one or more joints.

8. The method of claim 1, wherein implanting the electrical stimulation lead comprises implanting a plurality of electrical stimulation leads.

9. The method of claim 1, further comprising increasing an activation threshold of a side-effect exhibiting neural structure relative to an activation threshold of the dorsolateral funiculus of the patient, wherein the electrical stimulation energy is applied to the dorsolateral funiculus of the patient while the activation threshold of the neural structure relative to the dorsolateral funiculus is increased, thereby treating the non-neuropathic condition without stimulating the neural structure.

10. The method of claim 1, wherein applying electrical stimulation energy comprises applying the electrical stimulation energy as a time-varying electrical energy having a frequency in a range of 2 to 30 kHz.

11. A method of treating a non-neuropathic condition, the method comprising:

applying electrical stimulation energy to a dorsolateral funiculus of a patient through one or more electrodes of an implanted electrical stimulation lead to treat the non-neuropathic condition; and increasing an activation threshold of a side-effect exhibiting neural structure relative to an activation threshold of the dorsolateral funiculus of the patient, wherein the electrical stimulation energy is applied to the dorsolateral funiculus of the patient while the activation threshold of the neural structure relative to the dorsolateral funiculus is increased to treat the non-neuropathic condition without stimulating the neural structure.

12. The method of claim 11, wherein the non-neuropathic condition is an inflammatory condition.

13. The method of claim 12, wherein the inflammatory condition comprises inflammation of a spinal cord of the patient.

14. The method of claim 13, wherein the inflammatory condition is selected from spondyloarthritis, spondylarthropathy, or lower back pain arising from spinal cord inflammation.

15. The method of claim 12, wherein the inflammatory condition comprises inflammation of a region of the patient peripheral to a spinal cord of the patient.

16. The method of claim 15, wherein the inflammatory condition is selected from fibromyalgia, migraine headache, irritable bowel syndrome, ankylosing spondylitis, Crohn's disease, rheumatoid arthritis, osteoarthritis, or other arthritis of one or more joints.

17. A method of treating an inflammatory condition, the method comprising:
   implanting an electrical stimulation lead in an epidural space of the patient near a dorsolateral funiculus of a patient, the electrical stimulation lead comprising a plurality of stimulation electrodes, wherein the electrical stimulation lead is implanted with at least three of the stimulation electrodes disposed lateral of a midline of a spinal cord of the patient in a selected single dorsal-lateral quadrant of the epidural space and adjacent the dorsolateral funiculus of the patient; and
   applying electrical stimulation energy to the dorsolateral funiculus of a patient using at least one of the at least three of the stimulation electrodes of the implanted electrical stimulation lead to treat the inflammatory condition.

18. The method of claim 17, wherein the inflammatory condition comprises inflammation of a spinal cord of the patient.

19. The method of claim 17, wherein the inflammatory condition comprises inflammation of a region of the patient peripheral to a spinal cord of the patient.

* * * * *

UNITED STATES PATENT AND TRADEMARK OFFICE
CERTIFICATE OF CORRECTION

PATENT NO. : 9,168,378 B2  
APPLICATION NO. : 14/529969  
DATED : October 27, 2015  
INVENTOR(S) : Bradley Lawrence Hershey Page 1 of 1

It is certified that error appears in the above-identified patent and that said Letters Patent is hereby corrected as shown below:

Title Page, Item (63), in column 1, under "Related U.S. Application Data" delete all listed information.

"Continuation-in-part of application No. 13/708,742, filed on Dec. 7, 2012, now Pat. No. 8,923,975.
Provisional Application No. 61/569,216, filed Dec. 9, 2011."

Signed and Sealed this
Twenty-second Day of March, 2016

Michelle K. Lee
*Director of the United States Patent and Trademark Office*